United States Patent
Faurie (10) Patent No.: US 11,911,271 B2
(45) Date of Patent: Feb. 27, 2024

(54) ASSEMBLY FOR REPLACING A HEART VALVE OR CORONARY ANGIOPLASTY ASSEMBLY INCLUDING A DELIVERY CATHETER WITH OR WITHOUT INTRODUCER

(71) Applicant: ELECTRODUCER, Meylan (FR)

(72) Inventor: Benjamin Faurie, Grenoble (FR)

(73) Assignee: ELECTRODUCER, Meylan (FR)

( * ) Notice: Subject to any disclaimer, the term of this patent is extended or adjusted under 35 U.S.C. 154(b) by 477 days.

(21) Appl. No.: 17/194,449

(22) Filed: Mar. 8, 2021

(65) Prior Publication Data

US 2021/0186696 A1 Jun. 24, 2021

Related U.S. Application Data

(63) Continuation of application No. 15/564,458, filed as application No. PCT/EP2016/057385 on Apr. 5, 2016, now Pat. No. 11,045,318.

(30) Foreign Application Priority Data

Apr. 7, 2015 (FR) .................................... 1552955
Jul. 10, 2015 (FR) .................................... 1556582

(51) Int. Cl.
*A61F 2/24* (2006.01)
*A61B 17/3207* (2006.01)
(Continued)

(52) U.S. Cl.
CPC .... *A61F 2/2436* (2013.01); *A61B 17/320758* (2013.01); *A61B 17/3468* (2013.01);
(Continued)

(58) Field of Classification Search
CPC .. A61F 2/2436; A61F 2/95; A61F 2002/9517; A61N 1/05; A61N 1/056;
(Continued)

(56) References Cited

U.S. PATENT DOCUMENTS 5,370,685 A 12/1994 Stevens
5,545,214 A 8/1996 Stevens
(Continued)

FOREIGN PATENT DOCUMENTS

WO 93/01768 A1 2/1993
WO 97/28807 A1 8/1997

OTHER PUBLICATIONS

"Registry of Transcatheter Aortic-Valve Implantation in High-Risk Patients", Gilard et al; the New England Journal of Medicine: p. 1705-1715 (2012); cited in the specification.
(Continued)

*Primary Examiner* — Robert A Lynch
(74) *Attorney, Agent, or Firm* — Pearne & Gordon LLP (57) ABSTRACT

The present application relates to an assembly for replacing a heart valve or coronary angioplasty assembly, including an insertion sheath (13) of an introducer (1) or a delivery catheter (1'), which is smaller in size than an introducer, intended for being inserted into an artery of a human body. The application involves integrating the metal substrate of an electrode of the cardiac stimulator directly into the sheath for insertion into the artery of a patient.

19 Claims, 8 Drawing Sheets

(51) Int. Cl.
    *A61B 17/34*     (2006.01)
    *A61N 1/05*     (2006.01)
    *A61B 17/00*     (2006.01)
    *A61B 17/22*     (2006.01)

(52) U.S. Cl.
    CPC .... *A61N 1/056* (2013.01); *A61B 2017/00044* (2013.01); *A61B 2017/00243* (2013.01); *A61B 2017/22097* (2013.01); *A61B 2017/22098* (2013.01)

(58) Field of Classification Search
    CPC .. A61N 1/0565; A61N 1/372; A61N 1/37205; A61N 1/37211; A61N 2001/0585; A61B 17/3468; A61B 17/320758; A61B 2017/00044; A61B 2017/00243; A61B 2017/22038; A61B 2017/22097; A61B 2017/22098; A61B 18/1492; A61B 2018/1497; A61B 2018/16; A61B 2018/162
    See application file for complete search history.

(56) References Cited

U.S. PATENT DOCUMENTS

| | | | |
|---|---|---|---|
| 5,733,323 | A | 3/1998 | Buck et al. |
| 5,814,097 | A | 9/1998 | Sterman et al. |
| 7,018,406 | B2 | 3/2006 | Seguin et al. |
| 7,892,281 | B2 | 2/2011 | Seguin et al. |
| 8,652,202 | B2 | 2/2014 | Alon et al. |
| 8,747,459 | B2 | 6/2014 | Nguyen et al. |
| 2006/0241704 | A1 | 10/2006 | Shuros et al. |
| 2007/0100232 | A1 | 5/2007 | Hiller et al. |
| 2009/0270941 | A1* | 10/2009 | Mokelke ............... A61N 1/056 604/533 |
| 2009/0299443 | A1 | 12/2009 | Mokelke et al. |
| 2009/0318992 | A1 | 12/2009 | Eidenschink et al. |
| 2009/0318993 | A1 | 12/2009 | Eidenschink |
| 2010/0022823 | A1 | 1/2010 | Goldfarb et al. |
| 2011/0040344 | A1 | 2/2011 | Mokelke et al. |
| 2011/0230928 | A1 | 9/2011 | Shuros et al. |
| 2011/0251683 | A1* | 10/2011 | Tabor ................... A61F 2/2436 623/2.11 |
| 2012/0010461 | A1 | 1/2012 | Goldfarb et al. |
| 2012/0130220 | A1 | 5/2012 | Maskara et al. |
| 2013/0172924 | A1 | 7/2013 | Mokelke et al. |
| 2013/0268014 | A1 | 10/2013 | Shuros et al. |
| 2014/0066693 | A1 | 3/2014 | Goldfarb et al. |
| 2014/0074227 | A1 | 3/2014 | Tabor |
| 2015/0039059 | A1 | 2/2015 | Mokelke et al. |
| 2016/0082248 | A1 | 3/2016 | Shuros et al. |

OTHER PUBLICATIONS

"Left Ventricular Guidewire Pacing to Simplify Aortic Balloon Valvuloplasty", Susanne Navarini et al; Catheterization and Cardiovascular Interventions 73: p. 426-427 (2009); cited in the specification.

"A novel Approach for Transcoronary Pacing in a Porcine Model", Roland Prodzinsky et al; Journal of Invasive Cardiology 24(9): p. 451-455 (2012); cited in the specification.

"Optimizing of Transcoronary Pacing in a Porcine Model", Konstantin M. Heinroth, et al, Journal of Invasive Cardiology 21, p. 634-638 (2009); cited in the specification.

International Search Report for Corresponding Application No. PCT/EP2016/057385 dated Jun. 22, 2016.

Written Opinion for Corresponding Application No. PCT/EP2016/057385 dated Jun. 22, 2016.

* cited by examiner

ASSEMBLY FOR REPLACING A HEART VALVE OR CORONARY ANGIOPLASTY ASSEMBLY INCLUDING A DELIVERY CATHETER WITH OR WITHOUT INTRODUCER

CROSS-REFERENCE TO RELATED APPLICATIONS

This application is a continuation that claims the benefit of U.S. non-provisional application Ser. No. 15/564,458, filed on Oct. 5, 2017, which is a 371 of PCT/EP2016/057385 filed on Apr. 5, 2016, and claims benefit to French Application Nos. 1552955 filed on Apr. 7, 2015 and U.S. Pat. No. 1,556,582 filed on Jul. 10, 2015 which are all incorporated herein in their entirety by reference thereto.

TECHNICAL FIELD

The present invention relates to an assembly for replacing a heart valve by a percutaneous route or to a coronary angioplasty assembly, comprising a valve delivery catheter and, if appropriate, an introduction device commonly referred to as an "introducer".

The present invention relates more particularly to improved assistance in the replacement by cardiac shutdown by means of a cardiac stimulator.

Although described with reference to the replacement of an aortic valve, the assembly according to the invention may be used as a coronary angioplasty assembly which optionally necessitates the placement of a prosthesis commonly referred to as a "stent", in particularly in an emergency situation or even in complex interventional procedures.

Similarly, although described with reference to the replacement of an aortic valve, the assembly according to the invention may also be used for replacing another valve of the heart, such as the tricuspid valve or the mitral valve.

Generally, the introducer and/or the delivery catheter of the assembly according to the invention may be implanted in a patient by a percutaneous route, more precisely by a transfemoral, transaortic, carotid or subclavian route.

PRIOR ART

A commonly known disease of the heart is that associated with calcified narrowing of the tricuspid valve or of the aortic valve, the latter being the valve which separates a cavity of the heart, namely the left ventricle, from the aorta and which, in the open position, allows the blood to flow from the heart to the rest of the body of a human being.

Severe or very severe narrowing prevents the aortic valve from opening normally and thus generates the disease also referred to as calcified aortic valve stenosis.

Treatment of this disease involves replacing the defective aortic valve.

Replacement of a defective aortic valve is most commonly performed by opening the chest, placing the patient under extracorporeal circulation, temporarily stopping the heart, and then opening the heart with the aim of removing the native valve and replacing the latter with an artificial or prosthetic valve.

These successive steps of the operation have the major disadvantages of entailing a relatively long period of hospitalization of the patient, of being complex and costly, and of being limited to only some of the patients affected, since the physician and/or surgeon often considers that so-called "open heart" surgery cannot be performed because it is too risky in light of the general state of the patient, especially on account of the heart having to be stopped and of extracorporeal circulation having to be provided.

To overcome this disadvantage, it has been proposed to replace a heart valve using a minimally invasive approach, but still requiring extracorporeal circulation. Mention may be made of the international patent applications WO 93/01768 and WO 97/28807, and of the U.S. Pat. No. 5,814,097, 5,370,685 or 5,545,214, which illustrate known minimally invasive techniques and also instruments for implementing these techniques.

However, it has been felt that the existing techniques are not entirely satisfactory and that they may be improved.

In particular, these techniques have the following major disadvantages:

they always require the patient to be placed under extracorporeal circulation; they are difficult to implement in practice;

they do not permit precise control of the diameter by which the native valve is cut, with a view to subsequent calibration of the prosthetic valve;

they entail risks of diffusion of fragments of the calcified native valve within the organism, which may lead to an embolism;

they entail risks of perforating the wall of the aorta or heart;

they entail risks of acute regurgitation of blood during the ablation of the native valve.

To overcome the drawbacks of these techniques, one approach has been the placement of artificial aortic valves, called percutaneous valves, inspired by the techniques of endovascular treatment that involve introduction of a catheter inside a blood vessel, such as the aorta.

Thus, the native aortic valve, which has been rendered defective by calcification, is replaced by an artificial valve without the need for the onerous heart surgery that is normally required as has been explained above.

An artificial valve may currently be put into place by different percutaneous routes: a transfemoral route, i.e. by introduction from the femoral artery to the heart, or a transapical route, or a transaortic route, or a carotid route, or else a subclavian route, that is to say any route that does not require open heart surgery through an opening in the chest and that does not require extracorporeal circulation.

The operation itself involves placing an artificial valve (prosthesis), which reproduces the general shape of a normal native aortic valve, at the region of the calcified (diseased) native aortic valve, the latter being left in place and crushed by the prosthesis.

To do this, the artificial valve made of pericardium, a fine membrane surrounding the heart, of porcine or bovine origin, is fixed beforehand to the interior of a tubular and radially expansible metal mesh, called a stent, which is composed of an arrangement of wires made of shape-memory material, for example nickel-titanium alloy or cobalt-chromium alloy, or stainless steel 316L for coronary stents.

The assembly composed of valve and mesh is then compressed at the end of a tubular sheath, called a delivery catheter, which may be introduced either directly into an artery or into the inside of an introducer permitting access to the artery while maintaining hemostasis.

An interventionalist then slides the assembly composed of valve and mesh into the introducer or directly into the delivery catheter until said assembly arrives at the diseased aortic valve. Before being fitted in place, the assembly composed of valve and mesh is then placed at the region of the diseased valve by inflation of a balloon.

There are also valve delivery catheters comprising an assembly composed of valve and mesh without a balloon, in which catheters the valve is self-expanding, permitting placement of a valve which expands radially by simple retraction of the sheath surrounding it, and therefore without having to inflate a balloon beforehand.

For further details, reference may be made to the U.S. Pat. Nos. 7,018,406, 7,892,281, 8,652,202 and 8,747,459.

During the placement proper, it is necessary to temporarily arrest the heart for a short period by rapid ventricular stimulation in order to minimize the flow across the valve, i.e. between valves, and to avoid or at least reduce the potential embolization.

This temporary arrest of the heart, also commonly referred to as "cardiac shutdown", thus involves having the heart beat at 150 to 200 beats per minute such that there is no longer any effective contraction, which leads to a drop in the pressures and simulates ventricular tachycardia or fibrillation and then stabilization of the heart.

This stabilization of the heart permits the stabilization of the balloon and thus increases the precision of placement of the artificial valve in a matter of a few seconds.

There are bipolar stimulation catheters, with two electrodes, referred to as electrosystolic stimulation probes, for temporary intracardiac stimulation of the right ventricle.

These electrosystolic stimulation probes have a number of disadvantages, as are set out below.

Firstly, such a probe constitutes a central venous access with an added risk of vascular complication in the targeted population of patients. The French registry "France 2", which lists the aortic valve replacement operations, currently designated by the English language acronym TAVI (Transcatheter Aortic Valve Implantation), has indicated a rate of risk of substantial vascular complications equal to 4.7%. This result is reported on page 1709 of publication [1].

Secondly, this probe is relatively rigid. Hence, its placement in the right ventricle, which is fragile and whose wall is finer than that of the left ventricle, poses a considerable risk of the phenomenon well known to interventionalists under the term "tamponade", which is a manifestation of substantial circulatory insufficiency, which may even lead to the death of the patient.

It should also be noted that this risk exists both during the intervention, that is to say during the placement of the electrosystolic probe, and also in the post-operative period, on account of the mobilization of the patients in their beds and therefore of the probe which is still present and which may then pierce the wall of the right ventricle.

Moreover, there is a risk of the electrosystolic stimulation probe moving at the crucial moment of placement of the valve. This is because a stimulation probe is not fixed in a wall of the heart and may therefore move and thus generate a loss of capture of the electrical stimulation signal.

The heart is then no longer stimulated and therefore performs substantial movements, which impede the placement of the valve or of the balloon.

Another risk associated with the use of such probes is the risk of infection at the puncture site. The registry France 2 has indicated a rate of less than 1%: see publication [1].

Finally, an interventionalist does not consider as negligible the additional operating time associated with the placement of a temporary stimulation probe, which is an operation that is not always easy to perform.

Publication [2] puts forward the advantages of performing this ventricular stimulation on the left ventricle and not on the right ventricle and of doing so not by means of a specific transvenous stimulation catheter but by using an external cardiac stimulator with the guide wire used for interventions of this type.

Thus, the recommended technique described in publication [2] involves using the guide wire which supports the stent expansion balloon and is introduced into the left ventricle, as a part connected to the cathode of a cardiac stimulator, and a cutaneous electrode or needle inserted in the subcutaneous tissue as a support for the anode of the cardiac stimulator.

Publications [3] and [4], in the case of a coronary angioplasty intervention on a pig population, validates the efficacy of temporary cardiac stimulation with a lower stimulation voltage, in which the guide wire supporting the stent expansion balloon is used as a part connected to the cathode of a cardiac stimulator, and a cutaneous electrode or needle inserted in the subcutaneous tissue is used as a support for the anode of the cardiac stimulator.

Thus, these recommended techniques have the advantages of avoiding the need to implant an additional dedicated catheter, of avoiding an additional access to the heart, of reducing the time and cost of the operation, but also of reducing the rate of complications associated with the implantation of the dedicated catheter, all of this while permitting a stimulation that is equal to that achieved by transvenous stimulation.

Moreover, compared to the electrosystolic stimulation probes for the right ventricle, which pose the risk of tamponade as explained above, the guide wire used for this technique is very stable and bears permanently against the relatively thick wall of the left ventricle, since it serves as a rail for advancing the stent/balloon/valve assembly through the valve.

This being so, this technique nonetheless requires the placement of an additional electrode or subcutaneous needle, which has to be precise, and the placement and retention of crocodile clips on two supports spaced apart from each other.

There is therefore still a need to improve the operation of replacement of a heart valve that requires temporary shutdown during placement of the artificial valve, particularly in order to make the placement and manipulation of the cardiac stimulator electrodes quicker and easier for the surgeon(s) in charge of the operation.

The object of the invention is to respond at least in part to this need.

SUMMARY OF THE INVENTION

To do this, the invention relates, according to a first alternative, to an assembly for replacing a heart valve by a percutaneous route, comprising:

a device forming an introducer comprising at least one tubular insertion sheath, intended to be introduced into an artery of a human body and to allow the passage of a surgical intervention device such as a valve delivery catheter, and at least one electrically conductive element, of which a distal portion is exposed on at least one part of the outer periphery of the sheath in such a way as to be in contact with the subcutaneous tissue of the body or with the artery, and of which a proximal portion is accessible from the outside of the body in such a way as to serve as connection to one electrode of a cardiac stimulator;

at least one guide wire intended to be introduced into the tubular sheath of the introducer for advancing an artificial valve intended to replace the heart valve, the guide wire comprising a metallic part serving additionally as connection to the other electrode of the cardiac stimulator.

According to a second alternative, the invention relates to an assembly for replacing a heart valve by a percutaneous route, comprising:

a device forming a valve delivery catheter comprising at least one tubular insertion sheath, intended to be introduced into an artery of a human body, and at least one electrically conductive element, of which a distal portion is exposed on at least one part of the outer periphery of the sheath in such a way as to be in contact with the subcutaneous tissue of the body or with the artery, and of which a proximal portion is accessible from the outside of the body in such a way as to serve as connection to one electrode of a cardiac stimulator;

at least one guide wire intended to be introduced into the tubular sheath of the delivery catheter for advancing an artificial valve intended to replace the heart valve, the guide wire comprising at least one metallic part serving additionally as connection to the other electrode of the cardiac stimulator.

According to one embodiment, the electrode of the cardiac stimulator connected to the electrically conductive element of the introducer or of the delivery catheter is the anode, while the electrode connected to the metallic part of the guide wire is the cathode.

Thus, the invention essentially consists in integrating the metal support of an electrode of the cardiac stimulator directly in the sheath for insertion into the artery of a patient.

This insertion sheath may be that of an introducer, or directly that of a delivery catheter of reduced size compared to that of an introducer. A valve delivery catheter does not in fact require an introducer, since it may be introduced directly into the artery of a patient.

In other words, a cardiac stimulation support function is added to an introducer or to a delivery catheter whose basic function is to penetrate inside an artery of a patient in order to permit the passage of a valve/stent/balloon assembly, or an assembly composed of self-expansible valve and stent, for replacing a defective aortic valve.

By virtue of the invention, it is no longer necessary to insert a needle into the subcutaneous tissue, or a cutaneous electrode, to serve as a support for the electrode, typically the anode of a cardiac stimulator.

It is also no longer necessary to use and fit in place an electrosystolic probe according to the prior art, commonly called a temporary probe.

Moreover, by virtue of the invention, the stimulation intensity that is needed for cardiac shutdown is lower than in the solutions according to the prior art, on account of a lower impedance of the vascular system in relation to the subcutaneous tissue.

The electrical conducting element is advantageously a metal wire or strip which is accommodated at least in part within the thickness of the sheath and of which a distal portion is exposed at the outer periphery of the sheath.

The one or more surgeons in charge of the operation are thus able to easily connect the electrode, typically the anode of the cardiac stimulator, to a proximal portion of the metal wire or strip at the periphery of the introducer or of the delivery catheter, then to connect the other electrode as usual, typically the cathode, to the guide wire of the valve-stent-balloon assembly or of the assembly composed of self-expanding wire and stent.

In an assembly according to the invention, provision is made that another portion of metal wire or strip, distal from the one on which the electrical connection is made, and outside the body of the human being on whom the operation is performed, is exposed, that is to say not covered by the tubular insertion sheath, in order to be directly in contact with the subcutaneous tissues of the body or with the vascular space.

Thus, the step for preparing for shutdown of the heart is simpler and quicker to carry out.

Moreover, the inventor considers that an introducer according to the invention or a delivery catheter according to the invention may reduce the risks of complications associated with the electrosystolic stimulation probes according to the prior art which are placed in the right ventricle.

The introducer or the delivery catheter according to the invention may be introduced by a transapical route or by a transfemoral route, the latter being preferred since it is less invasive for weakened patients.

The introducer or the delivery catheter according to the invention may incorporate a peripheral perfusion system usually called a flush, which may be put in place in order to clear any possible blood clots from the interior of the introducer or of the catheter.

The introducer or the delivery catheter according to the invention may be formed on the basis of an already existing introducer or delivery catheter, respectively. It is only necessary to provide one additional production step which involves accommodating the metal wire or strip inside the insertion sheath and leaving the proximal and distal portions of the metal wire (strip) exposed.

Thus, for an assembly for replacing the aortic valve, the introducer may advantageously be produced on the basis of the same dimensions, shapes and materials as a known introducer, for example the one with the commercial name "Edwards eSheath insertion set", sold commercially by the company Edwards Lifesciences.

The artificial valve may be introduced and positioned in the artery by means of a delivery catheter according to the invention or by means of a conventional valve catheter, itself introduced into the introducer. The artificial valve then occupies a folded position and does not form an obstacle to the introduction and sliding of the valve catheter in the introducer and then in the artery, or in the delivery catheter according to the invention and then in the artery.

Then, in the deployed position, the artificial valve bears against the outer wall of the native heart valve in place of the latter and crushes it.

A conventional valve catheter or a valve catheter according to the invention thus makes it possible to introduce and position the artificial valve at the suitable location, in the same operating maneuver as the one carried out for opening and crushing the native valve. After opening and crushing of the latter, the valve catheter is slid axially in the distal direction in order to bring the artificial valve to the suitable location in the aperture of the native valve.

During the opening and crushing of the native valve, and thereafter, the one or more surgeons operating on the patients apply a cardiac stimulation by means of the external cardiac stimulator, the electrical current circulating between the cathode and the anode of the stimulator, the cathode being connected to the guide wire of the artificial valve and the anode being connected to the metal wire or strip integrated in the outer tubular sheath of the introducer or of the delivery catheter according to the invention.

Simultaneously with the ventricular stimulation, the artificial valve is deployed. The valve catheter is then withdrawn.

In summary, the advantages of an assembly according to the invention, compared to those of the prior art as presented in the preamble, are numerous, and the follow may be mentioned:

- simpler and quicker placement of an electrode, typically the ventricular stimulation anode, during the operation for replacement of a defective aortic valve;
- no need to insert an additional subcutaneous needle as support for an electrode, typically the anode, for the cardiac stimulator;
- reduced time and costs of the operation for replacement of a defective aortic valve;
- increased efficacy of the temporary stimulation with a view to performing the desired cardiac shutdown, on account of the lower impedance of the vascular system encountered by the electrical stimulation current since the metal wire or strip integrated in the introducer or in the delivery catheter is directly in contact with said system, in contrast to the needles of the prior art which come into contact with the cutaneous tissue of a patient, which necessarily has a higher impedance;
- increased efficacy of the temporary stimulation with a view to performing the desired cardiac shutdown on account of the stability of the rigid guide (diameter of the order of 1.455 mm) in the left ventricle, instead of the instability of the electrosystolic probe according to the prior art placed in the right ventricle;
- the possibility of performing temporary cardiac stimulation with a lower electric current on account of the lower impedance of the vascular system encountered between the two electrodes of the external stimulator;
- the elimination of the risks of complications associated with the temporary stimulation probes according to the prior art which are placed in the right ventricle;
- the possible use of the introducer or of the delivery catheter for several different types of TAVI interventions such as replacement of an aortic valve, pulmonary valve, tricuspid valve or mitral valve. In particular, for replacement of a degenerated tricuspid valve, only the technique of introducing a stimulation probe into the right ventricle by means of the guide rail (diameter 0.89 mm) is conceivable, since it is inconceivable to place both the guide rail and an electrosystolic probe because the expansion of the balloon or of the valve prosthesis would compress the probe, with the inherent risk of interrupting the stimulation or of wedging the stimulation probe;
- the possible use in the pediatric population during procedures performed on the valves or hearts which present greater tachycardia and are more mobile than in the adult population. Moreover, this is a population in which femoral venous puncture may be very difficult, likewise the placement of a stimulation probe in the right ventricle. Finally, the walls of the right ventricle in infants are thin and fragile, thereby increasing the risk of serious complications such as tamponade. This is also the population described in publication [2];
- the possible use in the field of emergency coronary angioplasty and in complex procedures in which temporary cardiac stimulation has to be carried out effectively and very quickly. To this end, an introducer or a delivery catheter according to the invention saves the time spent in placing an electrode or a supplementary subcutaneous needle as in the prior art, which may be crucial during these interventions.

According to an advantageous embodiment, the introducer or the delivery catheter according to the invention comprises:

- a distal notch formed within the thickness of the tubular sheath and leaving the distal portion of the metal wire or strip exposed, so as to produce the contact with a wall of the vascular system of the body;
- a proximal notch formed in a proximal zone of the introducer, intended to be outside the body, and leaving the proximal portion of the metal wire or strip exposed, so as to produce the connection to the electrode of the cardiac stimulator.

According to an advantageous variant in which the introducer or the delivery catheter comprises a rinsing device with faucets, called a flush, for rinsing the inside of the introducer by means of a suitable rinsing liquid, the proximal portion of the metal wire or strip is exposed at the level of the flush. This variant is advantageous in that it further simplifies the placement of the temporary stimulation, since the flush is directly oriented toward the external cardiac stimulator. Therefore, the placement and the retention of the connection clip may be done from the direction of the external stimulator. It is therefore easier for an interventionalist to control both the hold of the connection clip and the external cardiac stimulator. The proximal portion of the wire at the level of the flush may be configured as an electrical connector, on which it is possible to directly place a complementary connector connected directly to the external cardiac stimulator.

Preferably, the proximal notch and the proximal portion of the metal wire or strip are configured to allow a crocodile clip to be clipped onto said portion. It is thus possible to use these conventional clips without having to use clips that are specially designed for the introducer according to the invention.

More preferably, the distal portion of the metal wire or strip is arranged:

- either at a distance D, measured from the proximal end of the introducer, of between half and three quarters the height of the tubular portion of the sheath defining the proximal zone of the introducer;
- or at a distance of between 20 and 60 cm from the distal zone of the delivery catheter.

For the alternative with the valve catheter, an electrical contact zone at a distance of between 20 and cm from the distal zone of the catheter is advantageously able to ensure contact at the level of the intravascular endothelium of the aorta.

The cross section of the metal wire or strip is advantageously between 0.25 and 5 mm$^2$.

According to another advantageous embodiment of the invention, the electrically conductive element comprising an electrically conductive covering, such as a carbon covering, deposited on the outer periphery of the sheath.

According to this embodiment, the sheath is advantageously a two-layer covering with an electrically insulating inner layer and the electrically conductive layer deposited on the inner layer.

Preferably, the electrically conductive covering is deposited over the entire height of the outer periphery of the sheath, except for the distal end of the latter. This ensures definite contact between the electrically conductive covering and the subcutaneous tissue of the body or the wall of the femoral artery of the patient into whom the introducer or the delivery catheter according to the invention is introduced.

According to a particularly advantageous variant, the assembly comprises:
- a nozzle and, integrated within the latter, a ring in which the sheath is engaged with force,
- a connecting tongue made of electrically conductive material, of which one end is inserted through the ring in such a way as to establish an electrical contact with the electrically conductive covering, and of which the other end protrudes outside the nozzle, the surface of this end outside the nozzle being designed to be clamped by a connecting clip intended to be joined to an electrode of a cardiac stimulator. The formation of the assembly according to this variant is particularly effective since the electrical connection to the external cardiac stimulator is easily obtained with the aid of a clip which may be designed specifically to clip onto the connecting tongue. This makes the electrical connection reliable and allows an interventionalist to perform the connection easily and quickly.

The invention also relates to a guide wire for an assembly according to the invention as described above, comprising a metal core covered with an electrically insulated covering on a central portion of length L1, between the proximal end and the distal end of the guide wire, which metal core is not electrically insulated along the rest of the length of the guide wire.

Advantageously, the distal end not electrically insulated, and intended to come into contact with the wall of the left ventricle of a patient's heart, is more flexible than the rest of the guide wire.

Typically for a guide wire with a total length L of the order of 260 cm, the length L2 of the metal core not covered at the distal end and therefore not electrically insulated is of the order of 6 to 10 cm, the length L1 of the electrically insulating covering is of the order of 110 cm, the length of the metal core L3 equal to L−(L1+L2) not covered at the proximal end being of the order of 140 to 144 cm.

By keeping the periphery of the guide wire insulating only along the length L, but non-insulating at the distal and radial ends, emergency cardiac stimulation is permitted even in case of withdrawal of the delivery catheter. Indeed, in an emergency cardiac situation, the metal core may still serve as connection to an electrode, typically the cathode of the cardiac stimulator, and it is still possible to insert a needle into the subcutaneous tissues or leave the introducer according to the invention in place in order to serve as support for the other electrode, typically the anode of the cardiac stimulator. The electrical insulation between anode and cathode is then obtained by the insulating covering of the guide wire.

The guide wire according to the invention has many advantages, of which the following may be mentioned:
- it avoids the emergency use of an electrosystolic drive probe, the stimulation efficacy of which is not even guaranteed at 100%, in particular on account of the difficulties in fitting it in place within time constraints;
- it ensures the efficacy of the stimulation, which is not guaranteed with a guide wire according to the prior art, typically a metal guide wire with a Teflon covering which is not electrically insulated. The inventor has thus observed several stimulation failures when a catheter or balloon according to the prior art no longer insulates the guide wire;
- it permits the placement of an external cardiac stimulator and its drive probe calmly and without urgency since the stimulation is ensured between the guide wire according to the invention and the introducer or the delivery catheter according to the invention.

The invention also relates to the use of the assembly with introducer or delivery catheter described above for the replacement of an aortic valve, pulmonary valve, tricuspid valve or mitral valve.

Finally, the invention relates to the use of the assembly with introducer or delivery catheter described above for a coronary angioplasty intervention, particularly in an emergency situation.

This use is advantageous particularly in three intervention situations that may be encountered in coronary angioplasty.

The first is the treatment of an acute infarction which would cause conduction problems in the nature of extreme bradycardia or high-level atrio-ventricular block. Using an introducer according to the invention avoids the use of an electrosystolic probe according to the prior art, which is much more invasive and requires a not inconsiderable implantation time.

The second situation concerns the treatment of calcified coronary lesions by reaming inside the coronary vessels in question, usually with a reamer known by the tradename Rotablator®. Using an introducer according to the invention then also does away with the need to use an electrosystolic cardiac stimulation probe according to the prior art.

The third situation concerns the placement of a stent, in certain parts of the coronary vessels near their origins (ostia); these zones are very mobile with respect to the intervention catheter, but these anatomical zones require very great precision in the implantation of the stent. Using an introducer according to the invention makes it possible to stabilize the stent before and during its placement.

DETAILED DESCRIPTION

Other advantages and features of the invention will become clearer on reading the detailed description of the invention, which is given by way of a non-limiting example and with reference to the accompanying figures, in which.

In the description below, and in the whole of the present application, the terms "distal" and "proximal" are used with reference to the body of a patient whose defective native aortic valve is replaced by an artificial aortic valve. Thus, the distal end of an introducer is the end situated farthest inside the patient during the operation for replacement.

To simplify matters, the same elements in the device according to the invention and in the device according to the prior art are designated by the same references.

It should be noted that the various elements are not necessarily shown to scale.

Figure 1:
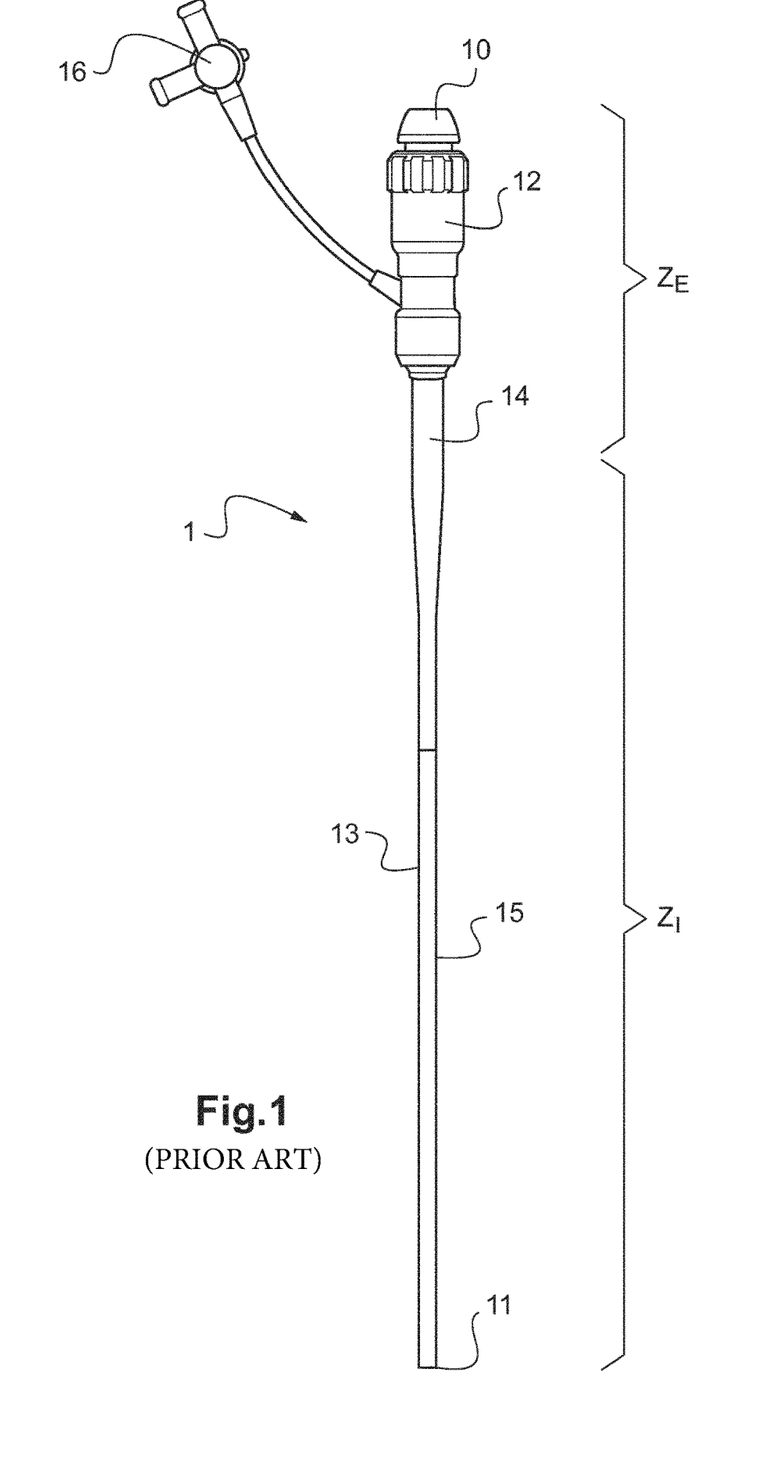
FIG. 1 is a perspective view of an introducer according to the prior art, intended to be introduced into a femoral artery in the groin region of a patient.

FIG. 1 shows an introducer 1 for replacing a heart valve by a transfemoral route.

Between its proximal end 10 and its distal end 11, this introducer 1 of generally tubular shape comprises a nozzle 12 which is continued by at least one outer tubular sheath 13 formed of two tubular portions 14, 15, from proximal to distal, considered with respect to the introduction into a femoral artery of a patient on whom an operation is to be performed, that is to say from the top downward in FIG. 1.

The nozzle 12 generally incorporates within it a set of leaktight valves to provide hemostasis, that is to say to ensure that the blood is retained inside the patient's blood vessels during the intervention.

The tubular sheath 13 may be extensible or non-extensible in order to allow the passage of a surgical intervention device such as a valve catheter, as is explained below. The material from which the sheath 13 is made is a biocompatible material such as silicone. It may also be made of Teflon® or of polyurethane. The sheath may advantageously be covered on the outside with a hydrophilic layer and on the inside with a layer having a low coefficient of friction in order to facilitate the sliding of an intervention device.

The introducer 1 illustrated in FIG. 1 likewise comprises an integrated rinsing device 16 with faucets, commonly referred to as a flush, for rinsing the inside of the introducer 1 by means of a suitable rinsing liquid.

All the elements of the introducer 1 that are present in the proximal or outer zone $Z_E$ are intended to remain outside the patient's body, while the entire distal portion 15 of the sheath 13 defining the distal zone $Z_I$ is intended to be introduced into a femoral artery of the patient.

The introducer 1 illustrated is, for example, the one sold commercially under the trade name "Edwards eSheath introducer set", which is sold commercially by Edwards Lifesciences.

Figure 2A:
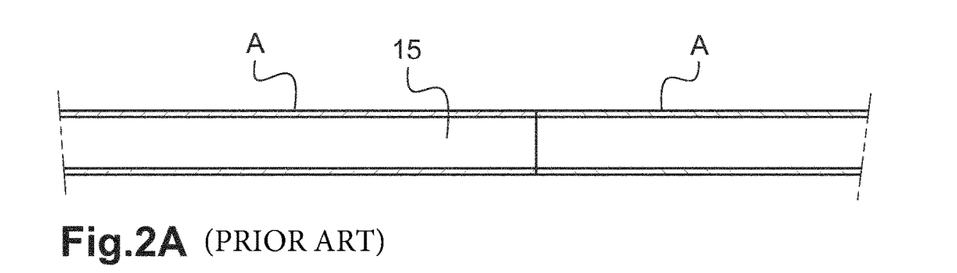
FIGS. 2A to 2C show, in partial longitudinal sectional views, various steps involved in sliding a valve catheter into the introducer according to FIG. 1, in order to fit an artificial valve in place as a replacement for a defective native aortic valve.
Figure 2B:
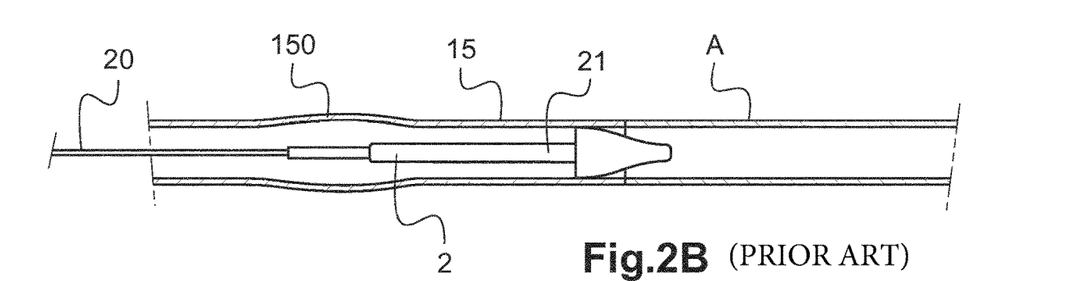
Figure 2C:
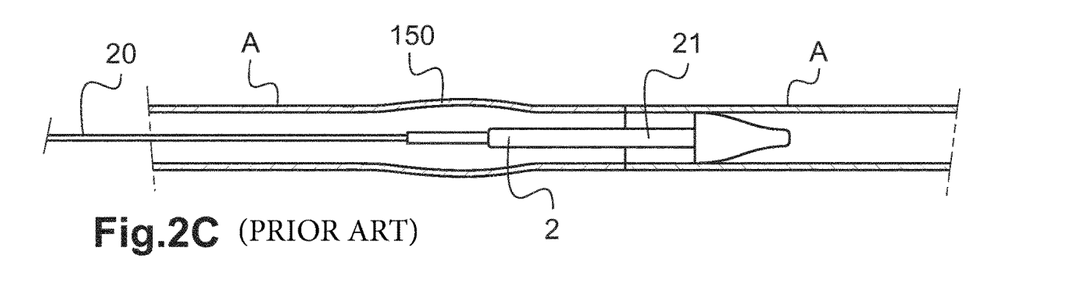

FIGS. 2A to 2C show the advance of a valve catheter 2, composed of a guide wire 20 and of an assembly 21 formed by an artificial valve fixed to a radial expansion stent and an inflatable balloon for effecting this expansion, inside the distal portion 14 of the tubular sheath of the introducer 1 already introduced into a femoral artery A.

The tip of the assembly 21 makes it possible to easily penetrate the deficient native aortic valve.

It will be seen from these figures that, the further the valve catheter 2 slides, the portion 15 of the tubular sheath temporarily deforms radially to form a slight protuberance 150. When the tubular sheath is not extensible, it does not deform radially.

Figure 3:
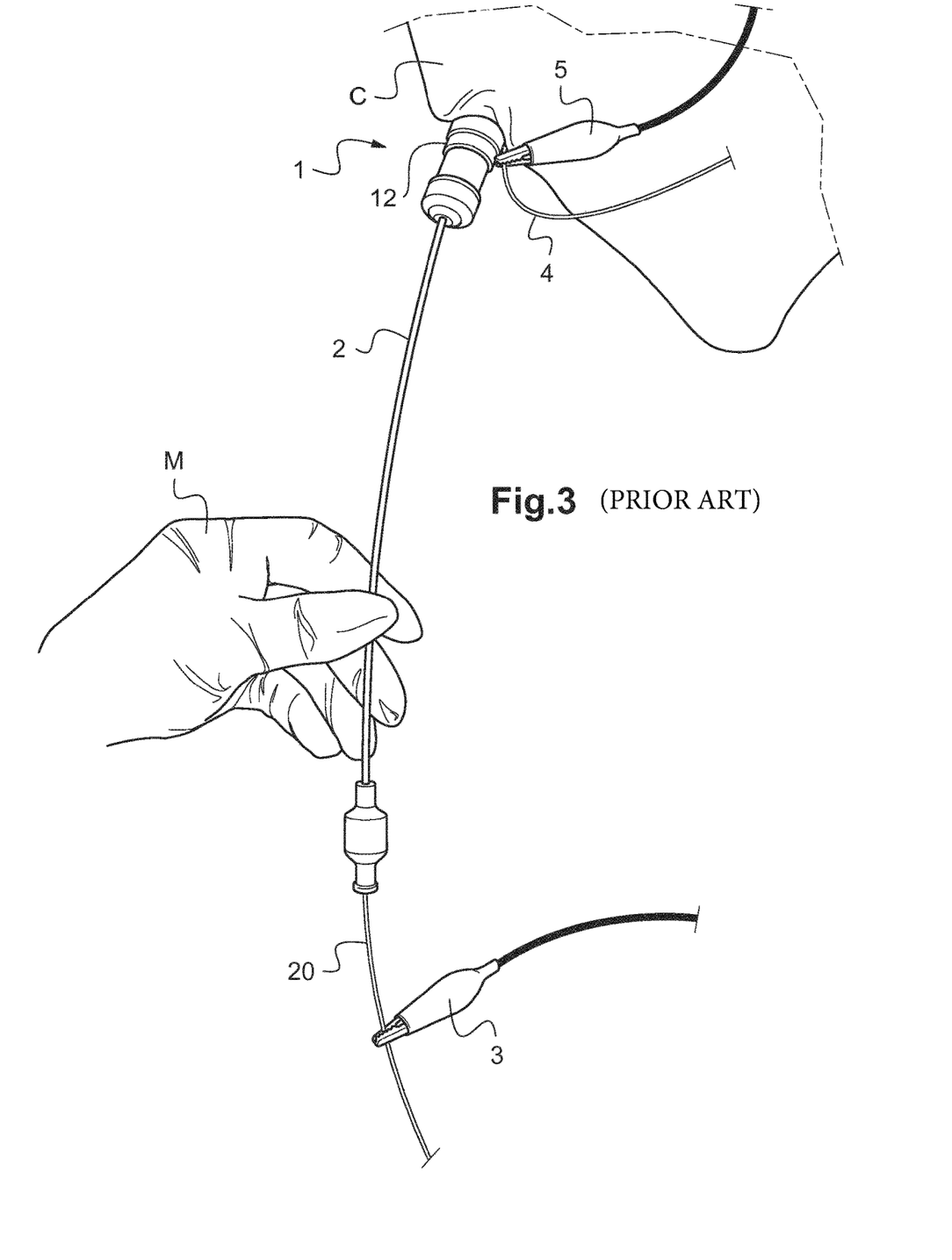
FIG. 3 shows, in a schematic perspective view from outside a patient, the step involving the placement of a valve catheter and of the cardiac stimulation electrodes according to the prior art.

It will be seen from FIG. 3 that the hand M of a surgeon introduces the valve catheter 2 into the introducer 1 already introduced into the femoral artery of a patient, with the nozzle 12 protruding outside of the body C.

This introduction of the valve catheter 2 allows the assembly 21 to be brought to the level of the deficient calcified aortic valve that is to be replaced.

Normally, as is likewise shown in FIG. 3, a clip 3 known as a crocodile clip is fixed by being clipped onto the guide wire 20 of the valve catheter 2. This clip 3 is connected to the cathode of a cardiac stimulator (not shown) situated outside of the body C.

A needle (not shown) is likewise inserted into the subcutaneous tissues of the body C of the patient on whom a procedure is to be performed. A metal wire 4 is fixed on this needle.

A crocodile clip 5 is likewise fixed by being clipped onto the metal wire 4.

This clip 5 is connected to the anode of the cardiac stimulator outside the body.

Thus, when the artificial valve is at the level of the natural aortic valve that is to be replaced, and before putting the artificial valve itself into place, i.e. before inflating the balloon and thus expanding the stent to which the valve is fixed, the surgeon first of all effects rapid ventricular stimulation of the left ventricle.

To do this, an electrical signal is delivered between the cathode and the anode by way of the clips 3 and 5, with the balloon serving as electrical insulator between these two electrodes.

Figure 4:
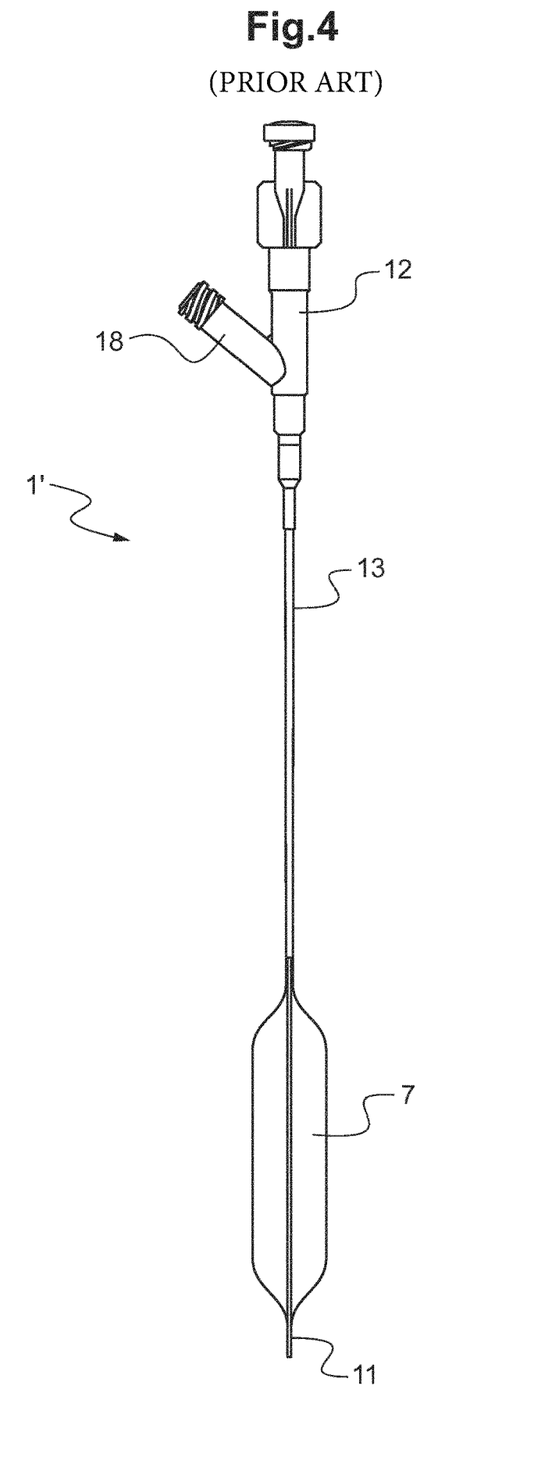
FIG. 4 is a schematic perspective view of a delivery catheter according to the prior art, intended to be introduced directly into the artery of a patient without the need for an introducer.

FIG. 4 illustrates a delivery catheter 1' which may be introduced directly into the artery of a patient without the need for an introducer. More precisely, the catheter 1' comprises a nozzle 12, which is continued by an insertion sheath 13. The nozzle 12 comprises a port 18 for inflation/deflation of a balloon 7 at the distal end 11, which makes it possible to expand a prosthetic valve (not shown).

Faced with numerous operations for replacing an aortic valve via a femoral route of the kind that has been briefly described, and in particular faced with the precise and delicate placement of the additional supplementary needle, and also the placement and retention of the connecting crocodile clips on two spaced-apart supports, the inventor of the present invention has thought to integrate the metal wire 4 directly in an introducer 1 or in a delivery catheter 1'.

Figures 5, 6:
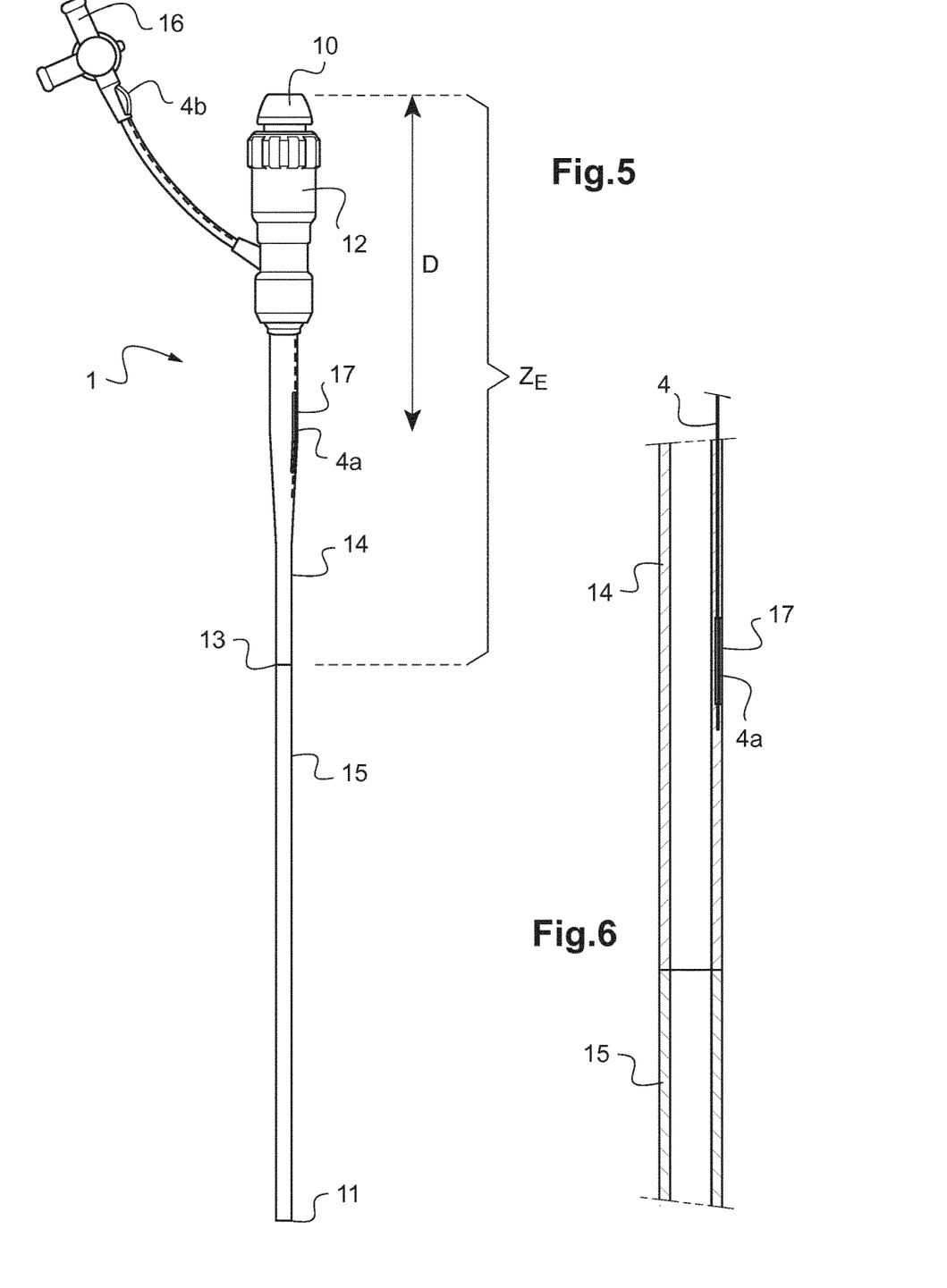
FIG. 5 is a perspective view of a device forming an introducer according to the invention.
FIG. 6 is a partial longitudinal sectional view of the tubular sheath of the introducer according to FIG. 5, showing the integration of a metal strip into the sheath in accordance with the invention.

More precisely, as is shown in FIGS. 5 and 6, the metal wire or strip 4 serving as connection to the anode of the cardiac stimulator is embedded at least partially within the electrically insulating and biocompatible material of the tubular sheath 13.

The metal wire or strip 4 may be produced in the form of a metal braid in order to give it the characteristics of flexibility that are necessary to accommodate the deformations of the extensible sheath during the introduction of a valve catheter into the introducer 1.

The metallic material of the wire or strip 4 is also chosen to be biocompatible, for example titanium, or a stainless steel optionally covered with a layer which is both anti-adhesive, in order to permit sliding inside the artery, and also conductive, in order to ensure electrical continuity between the core of the wire or strip and the subcutaneous tissue or the wall of the artery.

A distal notch 17 formed in the portion 15 of the tubular sheath leaves a distal portion 4a of the metal wire or strip 4 exposed. This distal portion 4a thus comes directly into contact with the subcutaneous tissue of the body or the wall of the femoral artery of the patient on whom an operation is performed.

It must of course be ensured that the exposed portion 4a, 4b of the metal wire or strip does not protrude outside the tubular sheath, so as not to risk causing injury during introduction of the catheter 1.

This distal notch 17 is positioned at a distance D from the distal end 11 so as to ensure that there is indeed contact between the distal portion 4a of the metal wire or strip 4 and the cutaneous tissue or the wall of the artery. More preferably, the distance D is such that the distal portion 4a is exposed in a zone corresponding to approximately the half length of the tubular portion 14. It is thereby ensured that there is contact with the vascular space, which may help improve the efficacy of the cardiac stimulation.

At the other end, a proximal notch is formed in a portion of the proximal zone $Z_E$ in order to expose a proximal portion 4b of the metal wire or strip 4, such that the latter is accessible from the outside of the body C.

At the level of the proximal notch, the metal wire or strip 4 and the notch 17 are configured in such a way that a connection clip, for example a crocodile clip 5, is fixed by being clipped onto the proximal portion 4b.

According to an advantageous alternative embodiment, illustrated in FIG. 5, the proximal portion 4b is exposed at the level of the flush device 16.

This variant is advantageous since the placement of the connection clip 5 is carried out at the side where the external cardiac stimulator is usually situated, which further facilitates the procedure for the interventionalist.

Figure 7:
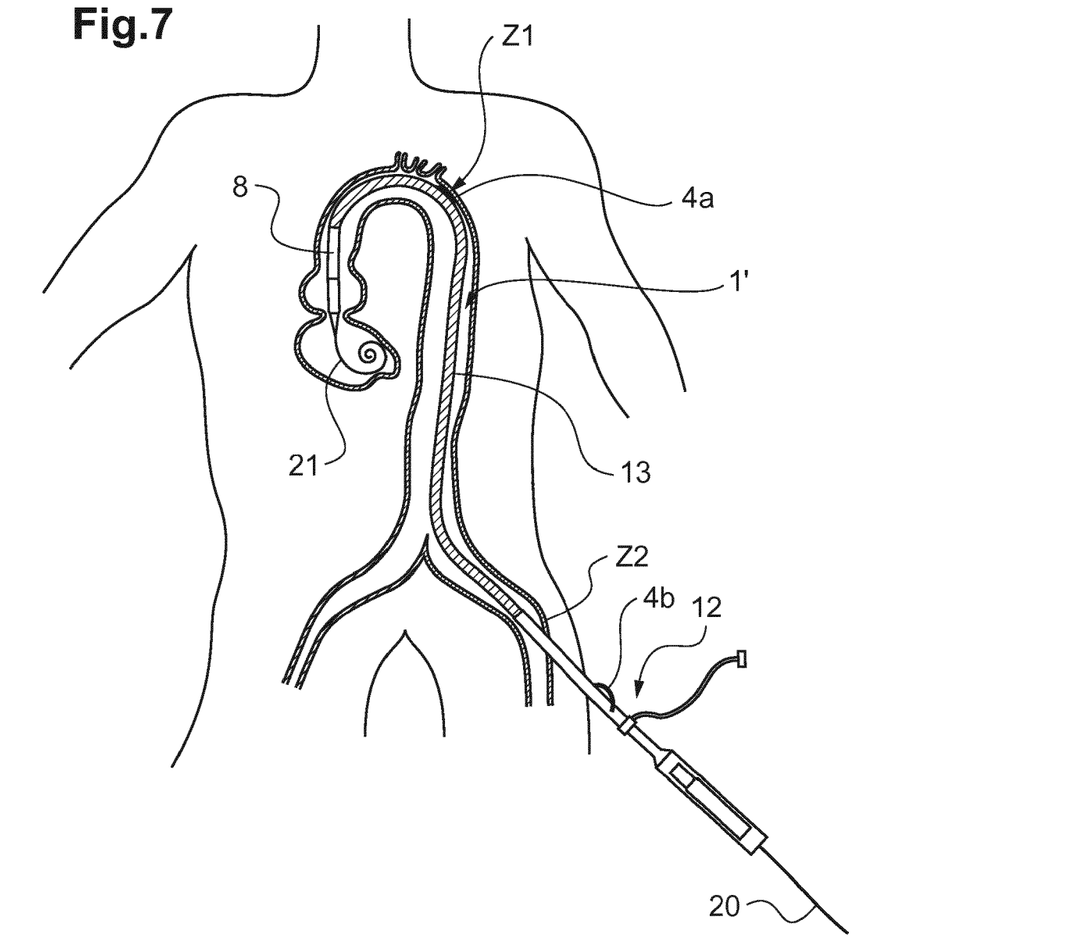
FIG. 7 illustrates the use of an assembly according to the invention with a catheter according to the invention introduced directly into an artery of a patient, the prosthetic valve being delivered from the catheter via the aortic arch.

FIG. 7 shows the use of an assembly with a delivery catheter 1' according to the invention for delivering a prosthetic valve 8 via the aortic arch of the patient.

As may be seen from FIG. 7, the catheter 1' introduced from the femoral artery at zone Z2 comes into contact with the aortic arch at zone Z1. The placement of the distal portion 4a of the metal wire or strip according to the invention is judiciously chosen such that this portion 4a touches the wall of the aortic arch in this zone Z1. For its part, the proximal portion 4b of the metal wire or strip is outside the body and exposed on a part of the nozzle 12 of the catheter.

Figure 8:
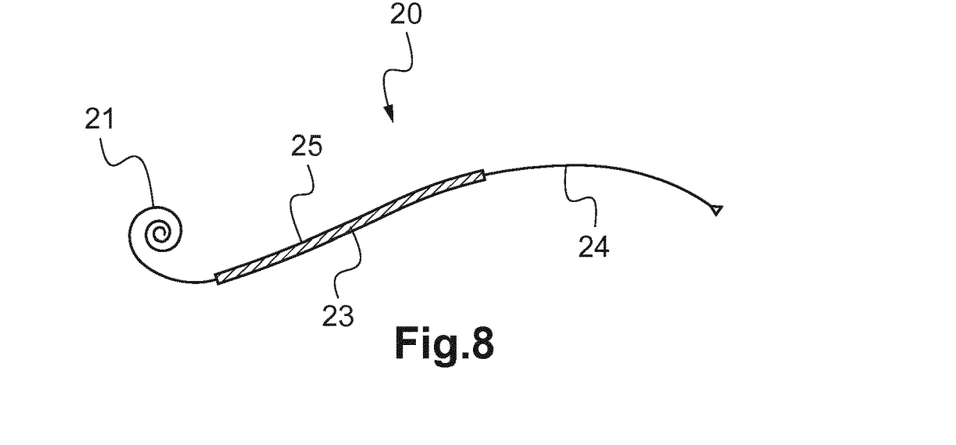
FIG. 8 is a schematic view of a guide wire according to an advantageous variant of the invention.

FIG. 8 shows a guide wire 20 according to an advantageous variant of the invention, which guide wire 20 may be introduced directly into a delivery catheter l' according to the invention as shown in FIG. 7, or into an introducer 1 according to the invention.

The guide wire 20 is formed along its entire length by a metal core which is covered by an electrically insulating cover 25 only in a central portion 23 of length L1, between the proximal end 22 and the distal end 24 of the guide wire. Since the metal core does not comprise an insulating cover on its periphery at its distal end 22 and proximal end 24, it is not electrically insulated along the rest of the length of the guide wire.

Advantageously, the distal end 22 not electrically insulated, and intended to come into contact with the wall of the left ventricle of a patient's heart, is more flexible than the rest of the guide wire. More precisely, as is shown in FIG. 7, the flexible distal end 22 coils up when it comes into contact with the endothelium of the left ventricle of the patient.

Thus, in an emergency situation in which it is necessary to stimulate the heart, it is always possible to insert a needle into the subcutaneous tissues if the catheter 1' is withdrawn or to leave the introducer according to the invention in place in order to serve as a support for another electrode, typically the anode of the cardiac stimulator.

It is thus entirely possible to provide effective stimulation, since the distal end 22 of the guide wire 20 always ensures electrical contact and, therefore, passage of current from the cathode, and the insulating cover 25 ensures complete insulation between the anode and the cathode along the intravascular trajectory.

The invention thus makes available an assembly with introducer or delivery catheter that may be used more particularly in the replacement of a heart valve by a percutaneous route, overcoming the disadvantages of the prior art and further improving the efficacy of the temporary cardiac stimulation in order to achieve the desired cardiac shutdown.

Indeed, the device according to the invention makes it possible to avoid the precise and delicate placement of a subcutaneous needle for connection to the anode of a cardiac stimulator.

The device according to the invention thus saves time in the replacement procedure.

In addition, the device according to the invention makes it possible to improve the inherent efficacy of the temporary stimulation in order to achieve the desired cardiac shutdown, since the impedance between the two electrodes of the cardiac stimulator is that of the vascular space, since the metal wire or strip comes into contact with the latter during the introduction of the sheath. On account of this impedance being lower than that of the cutaneous tissues encountered by the temporary stimulation probes according to the prior art, it is possible for the external stimulator to deliver an electrical stimulation current which is less than that according to the prior art, for a level of efficacy that is at least just as good.

The invention is not limited to the examples just described; it is possible in particular to combine features of the illustrated examples in variants that have not been illustrated.

Other variants and improvements may be provided without departing from the scope of the invention.

If, in the examples illustrated, the parts serving for connection to a stimulator, and integrated either in an introducer or in a delivery catheter, are exposed portions of a metal wire or strip, it is also conceivable instead to have a continuous covering on the insertion sheath surface that is electrically conductive.

This covering may be made in particular of a conductive carbon.

Figure 9:
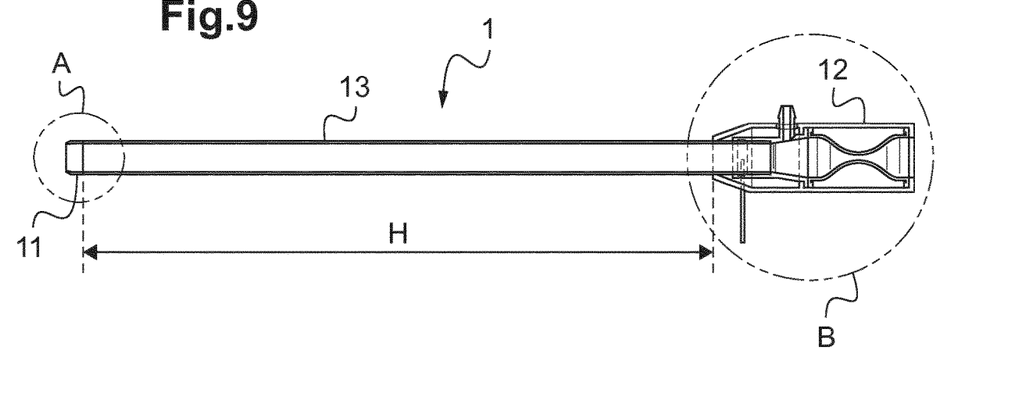
FIG. 9 is a longitudinal sectional view of an advantageous embodiment of a device forming an introducer according to the invention.
Figure 9A:
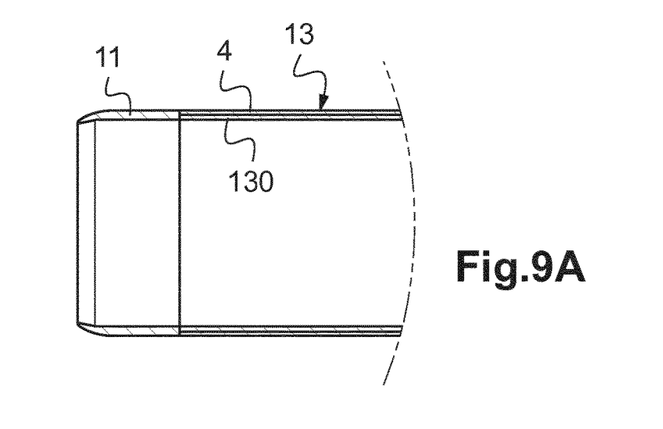
FIGS. 9A and 9B are details, according to A and according to B, of the distal end and proximal end, respectively, of the introducer according to FIG. 9.
Figure 9B:
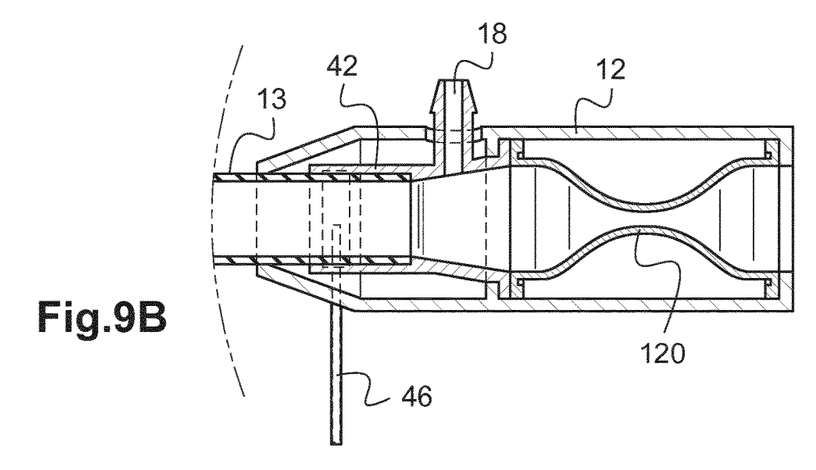

FIGS. 9 to 9B illustrate another advantageous embodiment of an introducer 1 according to the invention, having been a prototype by the inventor.

This introducer 1 comprises a two-layer covering with an electrically insulating inner layer 130 and an electrically conductive covering 4 deposited on the inner layer 130. This conductive covering 4 forms the conductive element intended to be in contact with the subcutaneous tissue of a patient's body. It may advantageously be a covering made of conductive carbon.

Preferably, as is illustrated in FIG. 9B, the electrically conductive covering is deposited over the entire height H of the outer periphery 130 of the sheath 13, except for the distal end 11 of the latter.

For its part, the proximal end of the introducer 1 comprises a nozzle 12 which incorporates within it a ring 42, in which the sheath 13 is engaged with force.

The nozzle 12 comprises in particular a valve 120 and a port 18 for fluidic purge by means of a suitable rinsing liquid.

The nozzle 12 likewise comprises a connecting tongue 46 which is made of electrically conductive material and of which one end is inserted through the ring 42, so as to establish an electrical contact with the electrically conductive covering 4, and of which the other end protrudes outside the nozzle.

In the example illustrated, the end of the tongue 46 outside the nozzle 12 extends transversely with respect to the axis of the introducer 1 when it is not constrained inside the body of a patient. This connecting tongue 46 is therefore designed to simplify the placement and retention of the connection clip 5, which may be done from the direction of the external cardiac stimulator. It is thus easier for an interventionalist to control the hold of both the connection clip and the external cardiac stimulator.

The surface of the end of the connecting tongue 46 outside the connector piece 12 is adapted to be clamped by a connection clip 5 intended to be connected to an electrode of a cardiac stimulator.

Figure 10:
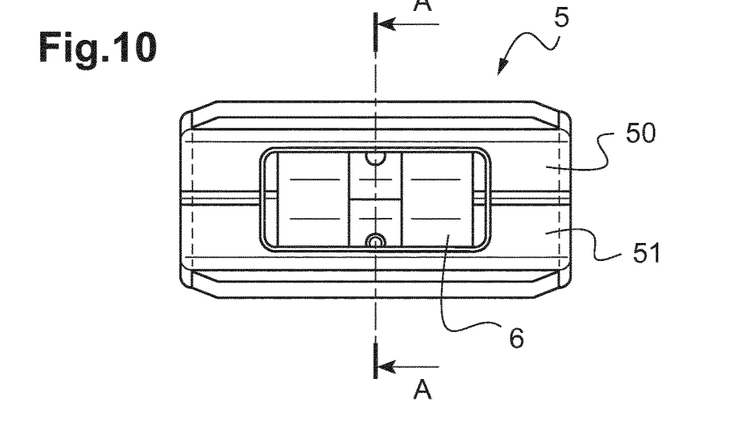
FIG. 10 is a front view of an electrical connection clip particularly designed for connection to the introducer of the invention according to FIGS. 9 and 9B.
Figure 10A:
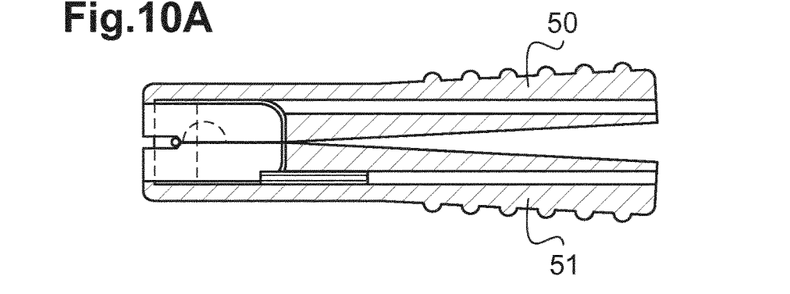
FIG. 10A is a longitudinal sectional view, along A-A, of the clip according to FIG. 10.

FIGS. 10 and 10A show a connection clip 5 which is particularly advantageous in terms of being ergonomic and compact and which may be clipped easily and reliably onto the connecting tongue 46.

This clip 5 comprises two electrically insulating branches 50, 51, which are articulated on each other, and accommodates a clip component 6 made of electrically conductive material.

Figures 11A, 11B, 12:
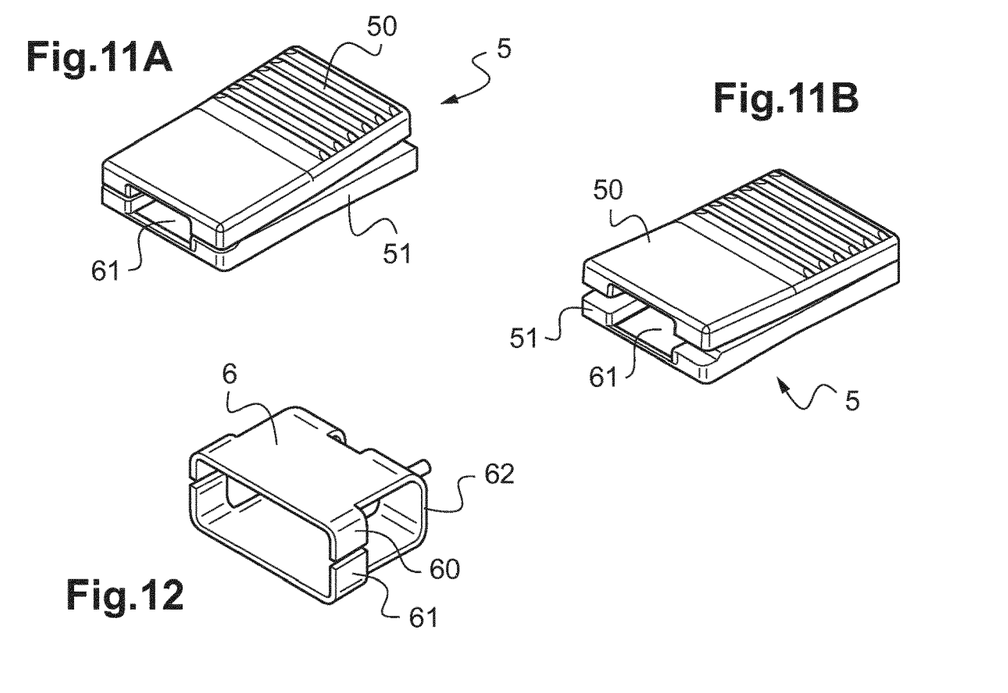
FIGS. 11A and 11B are perspective views of the clip according to FIG. 10, showing the clip in its closed position and its open position, respectively.
FIG. 12 is a perspective view of the clip element with jaws made of electrically conductive material, which clip element is integrated in the clip of FIG. 10 and is intended to be crimped on the connection part of the introducer according to the invention in order to produce the electrical connection.

As is shown in FIG. 12, this clip component 6 likewise comprises two branches 60, 61 which form jaws, connected to each other by a U-shaped bottom 62. The flexibility of this clip component 6 allows the branches 60, 61 to be spread apart from each other, while the absence of stress on the clip component 6 brings the branches 60, 61 into contact with each other.

Thus, simply by pressing manually on the branches 50, 51 of the clip 5, it is possible to bring the latter from its closed position (FIG. 11A), in which the jaws 60, 61 are able to clip around the connecting tongue 46 of the introducer in order to establish an electrical connection to the external cardiac stimulator, to its open position (FIG. 11B), which allows the clip 5 to be freed from the connecting tongue 46.

CITED REFERENCES

[1]: "*Registry of Transcatheter Aortic-Valve Implantation in High-Risk Patients*", Gilard et al.; the New England Journal of Medicine: pp. 1705-1715

[2]: "*Left Ventricular Guidewire Pacing to Simplify Aortic Balloon Valvuloplasty*", Susanne Navarini et al.; Catheterization and Cardiovascular Interventions 73: pp. 426-427 (2009)

[3]: "*A novel Approach for Transcoronary Pacing in a Porcine Model*", Roland Prodzinsky et al.; Journal of Invasive Cardiology 24(9): pp. 451-455 (2012)

[4]: "*Optimizing of Transcoronary Pacing in a Porcine Model*", Konstantin M. Heinroth et al., Journal of Invasive Cardiology 21, pp. 634-638 (2009)

The invention claimed is:

1. A method for replacing a heart valve of a patient's heart by a percutaneous route, the method comprising:
   introducing a tubular insertion sheath into an artery of the patient;
   contacting a subcutaneous tissue of the body or of the artery with an electrically conductive element provided at an outer periphery of a distal portion of the insertion sheath;
   introducing a guide wire into the insertion sheath for advancing an artificial valve intended to replace the heart valve of the patient's heart;
   positioning the distal portion of the insertion sheath having the electrically conductive element proximal to the distal end of the guide wire;
   contacting a wall of the left ventricle of the patient's heart with a distal end of the guidewire;
   introducing a surgical intervention device over the guide wire and into the insertion sheath including the artificial valve;
   connecting an electrode of a cardiac stimulator to a proximal end of the guide wire; and
   connecting another electrode of the cardiac stimulator external to the body so as to be connected only to the electrically conductive element and not to the guide wire.

2. The method of claim 1, wherein the distal end is not insulated and a portion of the guidewire adjacent and proximal to the distal end is insulated.

3. The method of claim 1, wherein the distal end of the guide wire has a greater flexibility than a portion of the guidewire adjacent and proximal to the distal end.

4. The method of claim 1, wherein the electrically conductive element is a distal portion of an elongated electrically conductive member extending through the insertion sheath from the electrically conductive element to a proximal end of the electrically conductive member disposed external to the patient.

5. The method of claim 1, wherein the electrically conductive element comprises an electrically conductive covering, deposited on the outer periphery of the insertion sheath.

6. The method of claim 1, wherein the electrically conductive element serves as an anode, and the guide wire serves as a cathode.

7. The method of claim 1, wherein the surgical intervention device is a guide catheter.

8. The method of claim 1, further including connecting a rinsing device to the insertion sheath or to the surgical intervention device at a location adjacent the connected another electrode.

9. The method of claim 1, further including connecting a clip that is connected to the another electrode at a notch provided at a proximal portion of an electrically conductive member extending from or disposed at a proximal end of the insertion sheath, the electrically conductive member including the electrically conductive element at a distal end thereof.

10. A method for replacing a heart valve of a patient's heart by a percutaneous route, the method comprising:
   providing a catheter device having a distal electrically conductive portion exposed at an external periphery of a distal portion of the catheter device spaced from a distal-most end face of the catheter device, and also having a proximal electrically conductive portion exposed at an external periphery of a proximal portion of the catheter device opposite the distal portion of the catheter device and in electrical communication with the distal electrically conductive portion;

providing a guide wire having a distal non-insulated end, a proximal non-insulated end, and an insulated section disposed therebetween;

inserting the catheter device into the patient and inserting the guide wire into the catheter device;

positioning the distal end of the guide wire spaced from the distal portion of the catheter device and in a different chamber or vessel of the patient's heart than the distal electrically conductive member; and electrically stimulating the patient's heart by connecting each of the proximal end of the guide wire and the proximal electrically conductive portion to a cardiac stimulator.

11. The method of claim 10, wherein the catheter device includes a two-layer covering with an electrically insulating inner layer and an electrically conductive covering deposited on the inner layer, and wherein the electrically conductive covering includes the distal electrically conductive portion.

12. The method of claim 11, wherein the electrically conductive covering is deposited over the entire length of the outer periphery of the insertion sheath, except for the distal-most end face and a portion directly proximal thereof.

13. The method of claim 10, wherein the distal and proximal electrically conductive portions are disposed at opposite ends of a metal wire or strip which is accommodated at least in part within the thickness of the catheter device.

14. The method of claim 13, wherein a cross section of the metal wire or strip is between 0.25 and 5 mm2.

15. The method of claim 10, wherein the distal electrically conductive portion is disposed at a distance of between 20 cm and 60 cm from the distal-most end face of the catheter device.

16. A method for replacing a heart valve of a patient's heart by a percutaneous route, the method comprising:
   inserting a distal end of a catheter device into the left ventricle of the patient's heart such that a discrete electrically conductive aspect located along the distal end of the catheter device is in contact with internal tissue of the left ventricle;
   inserting a distal end of a guide wire into the catheter device such that the distal end of the guide wire is in electrical communication with a chamber or vessel of the patient's heart;
   arranging the distal end of the guide wire and the electrically conductive aspect such that they are in electrical communication with one another only through tissue of the patient's heart and through a cardiac stimulator, thereby completing an electrical circuit including the patient's heart;
   inserting a replacement heart valve through the catheter device; and
   directing an electrical current through the electrical circuit when the replacement heart valve is disposed within the catheter device and insulated from the electrical circuit.

17. The method of claim 16, further including attaching a pair of clips separately to the guide wire and to the catheter device at respective notches external to the body configured to receive said clips.

18. The method of claim 17, further including orienting a flush device at the catheter device adjacent the respective notch of the catheter device.

19. The method of claim 16, further including engaging the catheter device within a ring integrated within a nozzle and inserting one end of a connecting tongue of electrically conductive material through the ring so as to be in electrical communication with the discrete electrically conductive aspect, and such that another end of the connecting tongue opposite the one end protrudes outside the nozzle and is electrically connectable to the cardiac stimulator.

* * * * *